(12) United States Patent
Song et al.

(10) Patent No.: US 10,675,612 B2
(45) Date of Patent: Jun. 9, 2020

(54) MOLYBDENUM OXIDE COMPOSITE AND PREPARATION METHOD THEREFOR

(71) Applicant: LG CHEM, LTD., Seoul (KR)

(72) Inventors: Cheolock Song, Daejeon (KR); Gyo Hyun Hwang, Daejeon (KR); Ara Cho, Daejeon (KR); Jungup Bang, Daejeon (KR)

(73) Assignee: LG CHEM, LTD., Seoul (KR)

( * ) Notice: Subject to any disclaimer, the term of this patent is extended or adjusted under 35 U.S.C. 154(b) by 0 days.

(21) Appl. No.: 15/510,170

(22) PCT Filed: Sep. 30, 2015

(86) PCT No.: PCT/KR2015/010326
§ 371 (c)(1),
(2) Date: Mar. 9, 2017

(87) PCT Pub. No.: WO2016/053004
PCT Pub. Date: Apr. 7, 2016

(65) Prior Publication Data
US 2017/0291166 A1 Oct. 12, 2017

(30) Foreign Application Priority Data
Oct. 1, 2014 (KR) .......................... 10-2014-0132699

(51) Int. Cl.
*B01J 23/881* (2006.01)
*B01J 35/02* (2006.01)
(Continued)

(52) U.S. Cl.
CPC ............. *B01J 23/881* (2013.01); *B01J 23/28* (2013.01); *B01J 35/0006* (2013.01);
(Continued)

(58) Field of Classification Search
CPC ...... B01J 23/28; B01J 23/881; B01J 35/0006; B01J 23/88; B01J 35/026; B01J 35/1009; B01J 35/1014; C07C 2523/28; C07C 2523/745
See application file for complete search history.

(56) References Cited

U.S. PATENT DOCUMENTS 3,152,997 A * 10/1964 Balcet ..................... C07C 45/38
502/316
4,024,074 A * 5/1977 Cairati ................. B01J 23/8876
502/311
(Continued)

FOREIGN PATENT DOCUMENTS

CN 1546232 A 11/2004
CN 103663560 A 3/2014
(Continued)

OTHER PUBLICATIONS

Jin, Guojie, et al.,"Fe2(MoO4)3/MoO3 nano-structured catalysts for the oxidation of methanol to formaldehyde," Journal of Catalysis, vol. 296, 2012, pp. 55-64.
(Continued)

*Primary Examiner* — Jun Li
(74) *Attorney, Agent, or Firm* — Dentons US LLP

(57) ABSTRACT

According to the present invention, a composite including amorphous iron molybdate islands, shows a smaller island size and a uniform distribution of islands compared with a conventional composite including crystalline islands, and thus has a higher specific surface area, thereby exhibiting excellent activity as a catalyst.

16 Claims, 15 Drawing Sheets

(51) Int. Cl.
*B01J 35/10* (2006.01)
*B01J 37/02* (2006.01)
*B01J 37/08* (2006.01)
*B01J 23/28* (2006.01)
*B01J 37/04* (2006.01)
*C01G 49/02* (2006.01)
*B01J 35/00* (2006.01)
*B01J 37/00* (2006.01)
*C07C 5/48* (2006.01)

(52) U.S. Cl.
CPC ......... *B01J 35/026* (2013.01); *B01J 35/1009* (2013.01); *B01J 35/1014* (2013.01); *B01J 37/009* (2013.01); *B01J 37/0221* (2013.01); *B01J 37/04* (2013.01); *B01J 37/08* (2013.01); *C01G 49/02* (2013.01); *C07C 5/48* (2013.01); *C07C 2523/28* (2013.01); *C07C 2523/745* (2013.01)

(56) References Cited

U.S. PATENT DOCUMENTS

| | | | |
|---|---|---|---|
| 4,912,182 A | 3/1990 | Castner et al. | |
| 7,572,752 B2 * | 8/2009 | Conca | B01J 23/002 502/304 |
| 10,130,937 B2 * | 11/2018 | Song | B01J 37/10 |
| 2012/0237828 A1 | 9/2012 | Tan et al. | |
| 2013/0209351 A1 | 8/2013 | Shin et al. | |
| 2014/0024525 A1 | 1/2014 | Lin et al. | |
| 2014/0171303 A1 | 6/2014 | Yoshida et al. | |

FOREIGN PATENT DOCUMENTS

| | | |
|---|---|---|
| KR | 1990-0003221 A | 3/1990 |
| KR | 10-2010-0042935 A | 4/2010 |
| KR | 10-2014-0002799 A | 1/2014 |
| KR | 10-2014-0008349 A | 1/2014 |
| WO | 2012/025737 A1 | 3/2012 |

OTHER PUBLICATIONS

"In situ diffusion growth of Fe2(MoO4)3 nanocrystals on the surface of a-MoO3 nanorods with significantly enhanced ethanol sensing properties"; Chen, et al; J. Mater. Chem., 2012, 22, 12900.

"Porous Iron Molybdate Nanorods: In situ Diffusion Synthesis and Low-Temperature H2S Gas Sensing"; Chen, et al.; ACS Appl. Mater. Interfaces 2013, 5, 3267-3274.

* cited by examiner

[Figure 1]
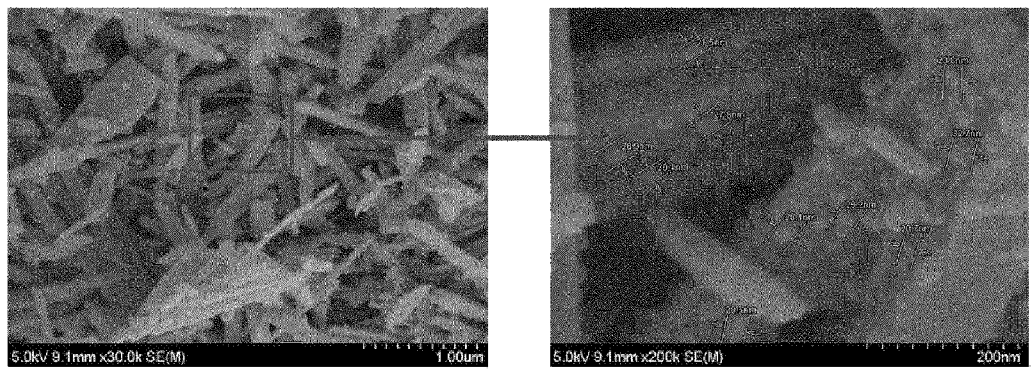

[FIG. 2]
(a)
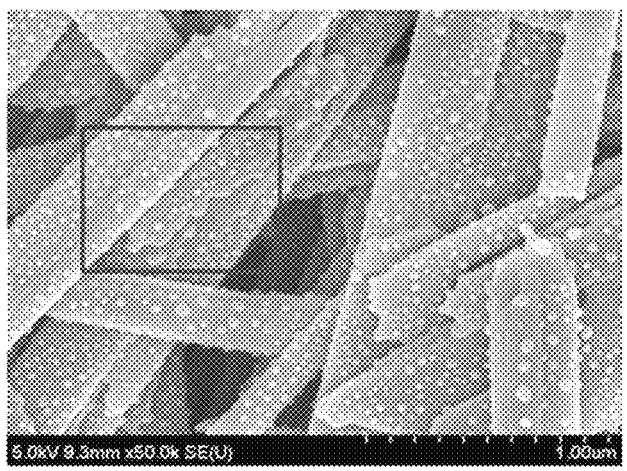
(b)
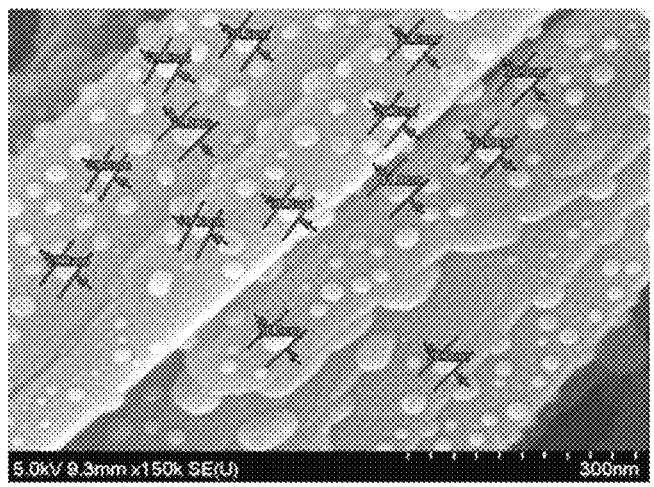

[FIG. 3]
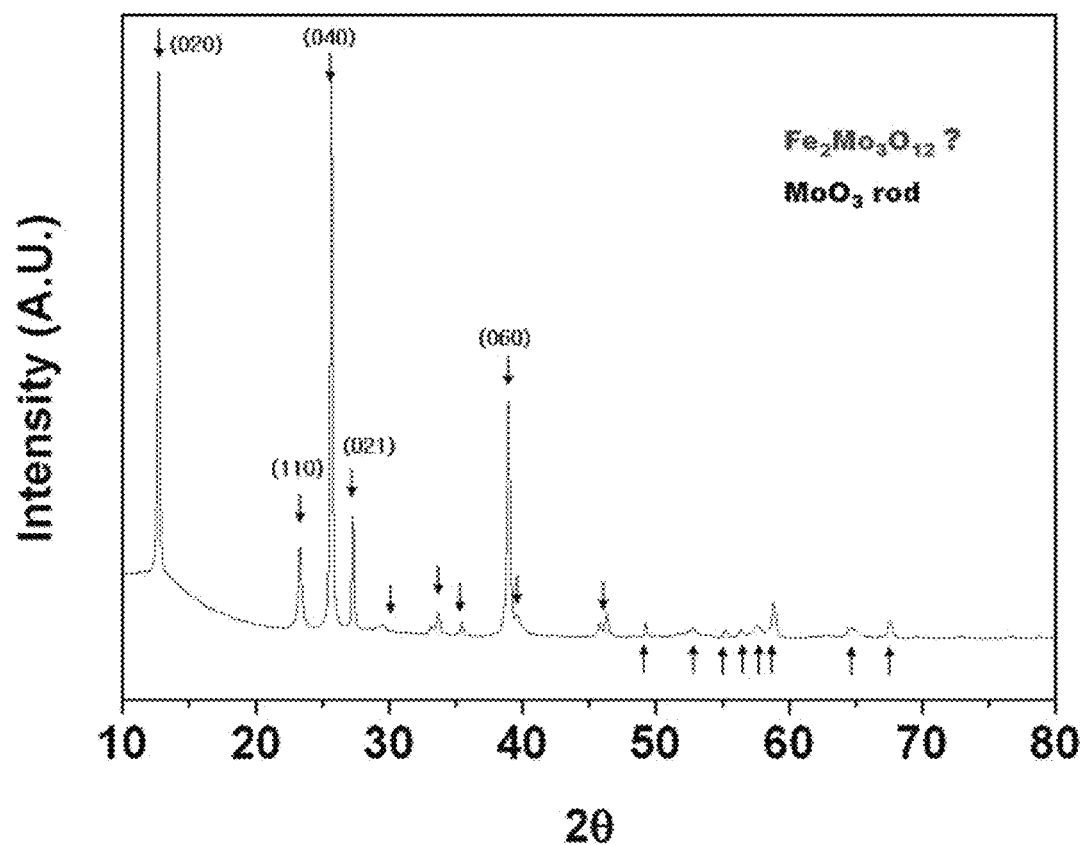

[FIG. 4]
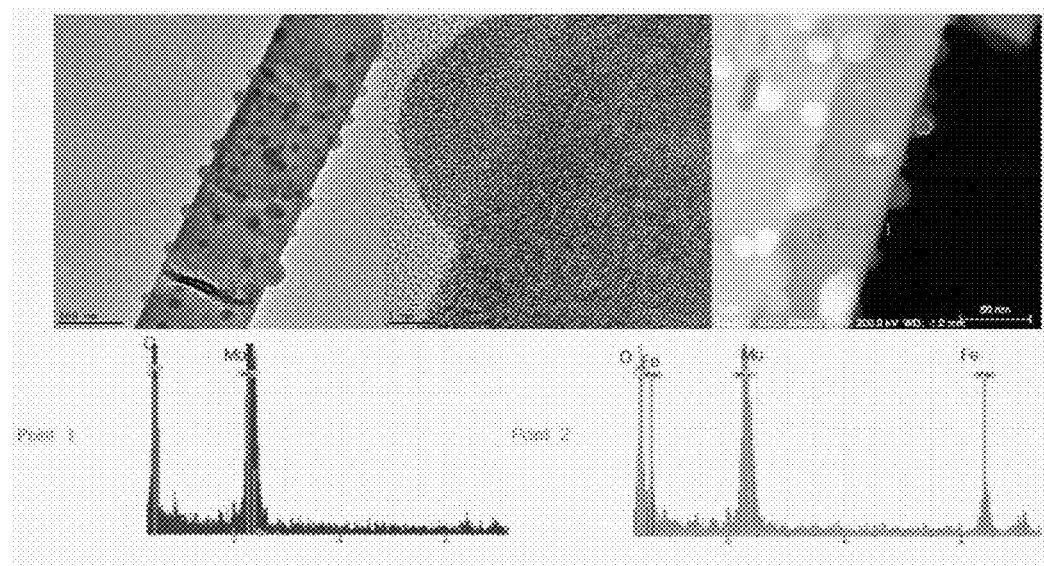
[FIG. 5]
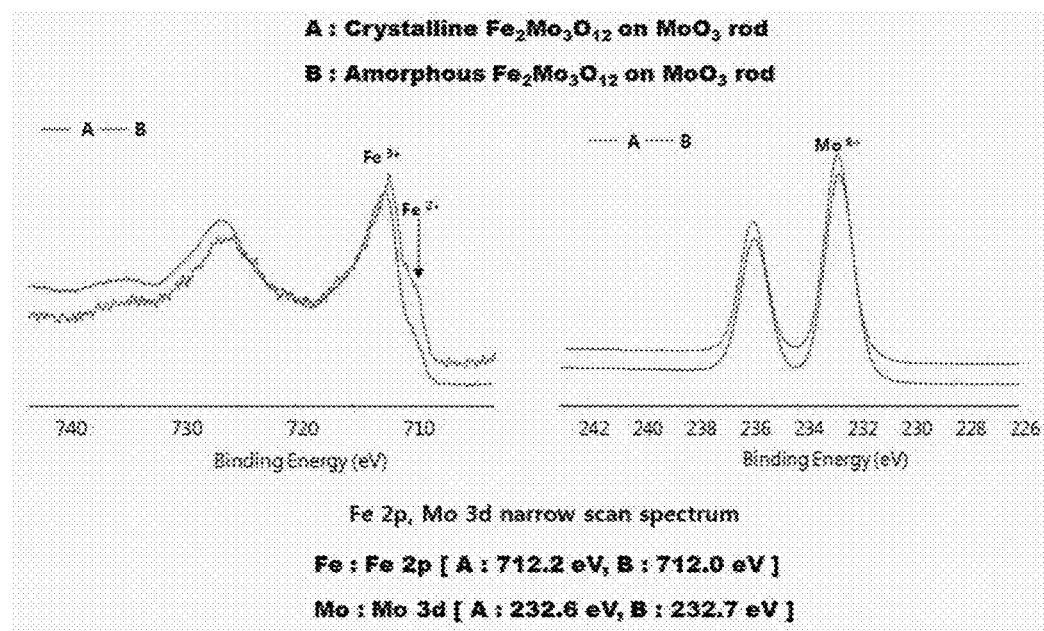

[FIG. 6]
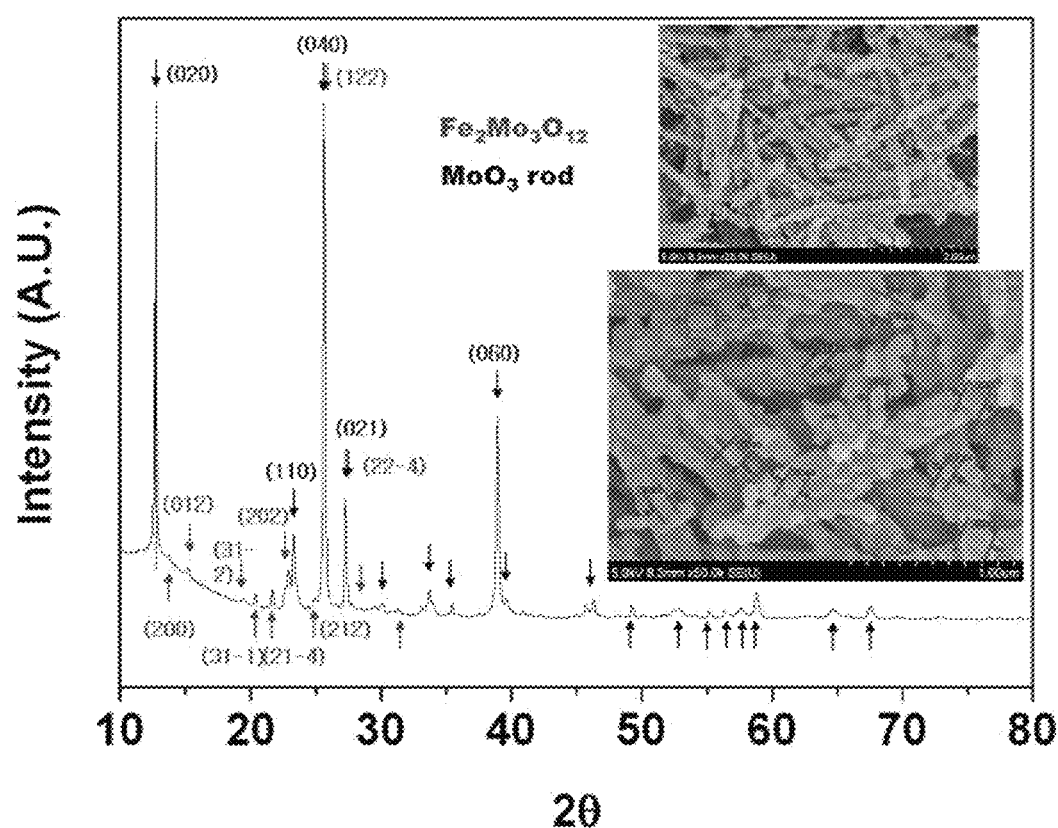

[FIG. 7]
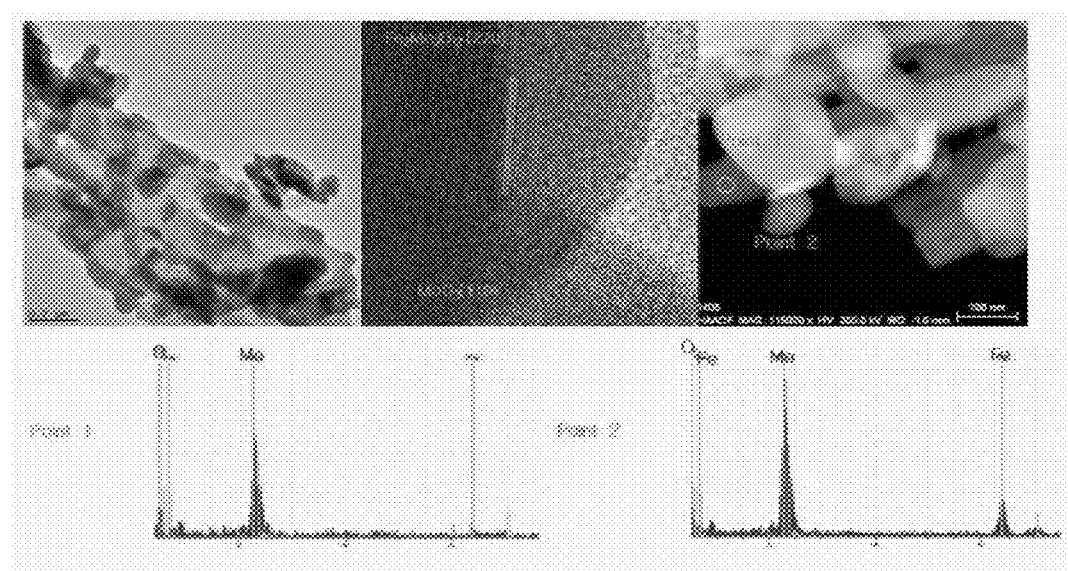

[FIG. 8]
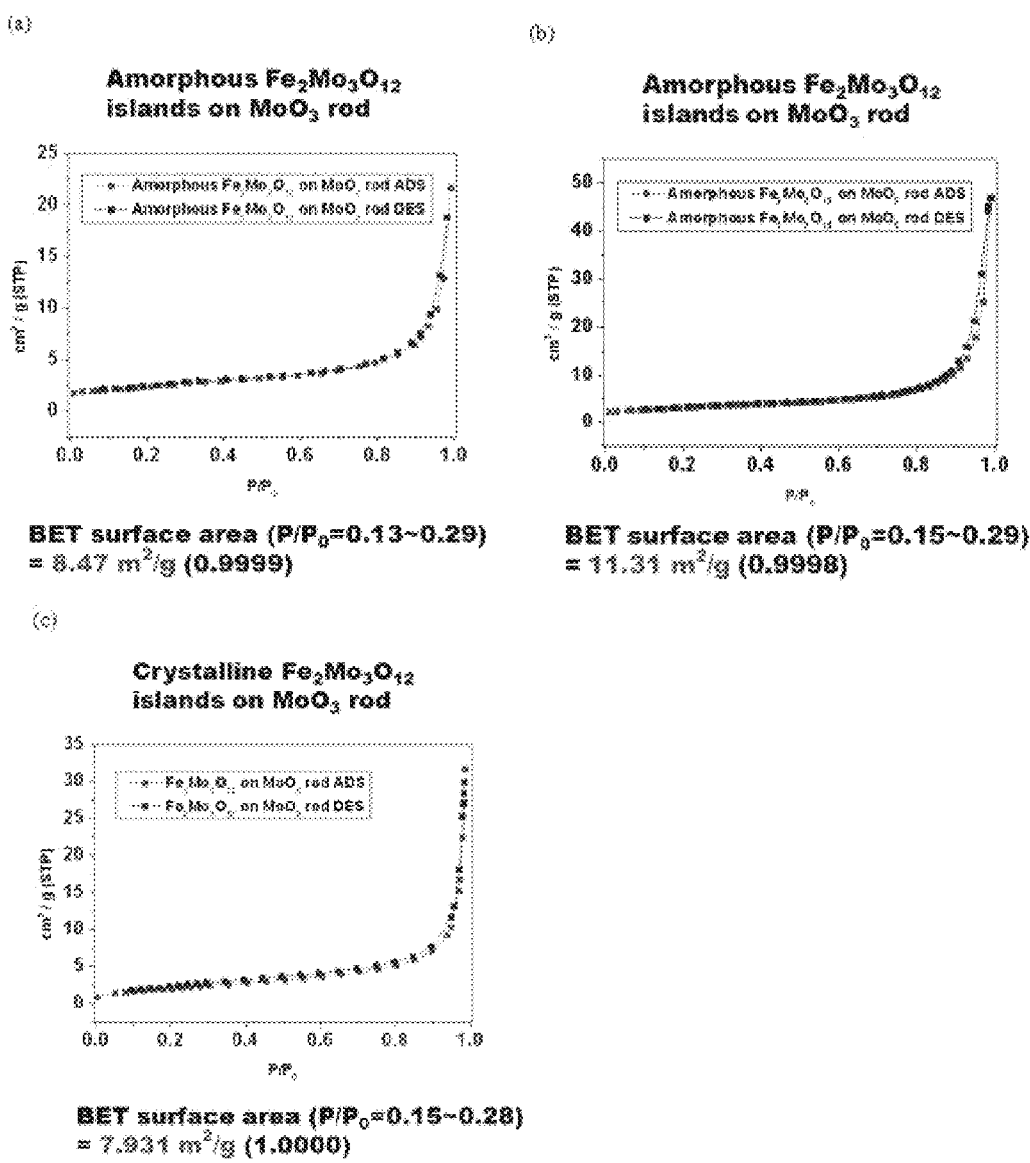

[FIG. 9]
(a)
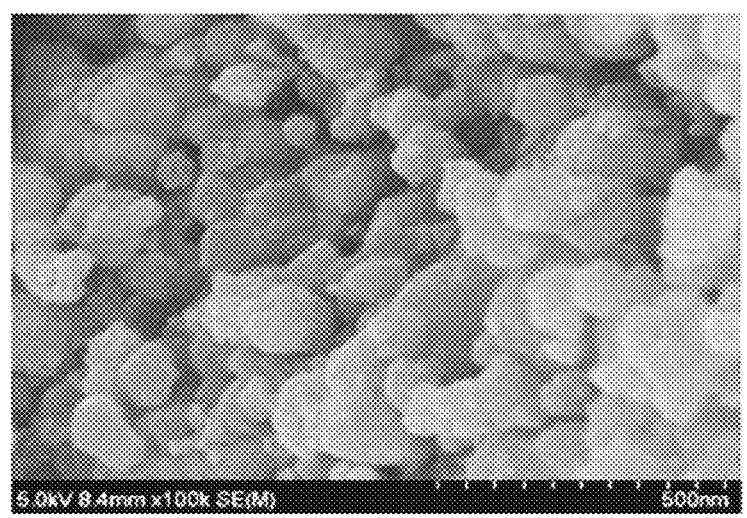
(b)
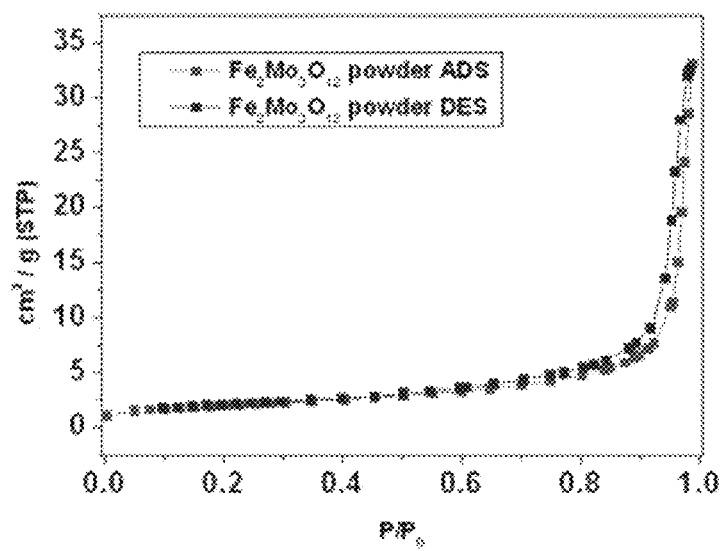
**BET surface area ($P/P_0$=0.15~0.28)
= 7.06 $m^2$/g (0.9999)**

[Figure 10]

| EQUIPMENT | ICP | |
|---|---|---|
| RESULT | CONTENT(wt %) | |
| | Fe | Mo |
| Amorphous $Fe_2Mo_3O_{12}$ islands on $MoO_3$ | 1.33 | 62.6 |

| | ICP | |
|---|---|---|
| | Norm. Fe | Norm. Mo |
| Amorphous $Fe_2Mo_3O_{12}$ islands on $MoO_3$ | 2.08 | 97.92 |

THEORETICAL CALCULATION OF PARTICLE RATIO OF MoO3 AND AMORPHOUS Fe2Mo3O12 WHICH ARE COMPONENTS OF Bi2Mo3O12 ISLANDS COMPOSITE ON ROD-SHAPED MoO3

Norm. Fe (2.07) = Particles (1) of $Fe_2Mo_3O_{12}$ * $Fe_2$ mol weight (55.85 * 2 g) of $Fe_2Mo_3O_{12}$
/ [ Particles (1) of $Fe_2Mo_3O_{12}$ * ($Fe_2$ and $Mo_3$ mol weight (55.85 * 2 g + 95.96 * 3 g) of $Fe_2Mo_3O_{12}$ + Particles (52) of $MoO_3$ * Mo mol weight (95.96 g) of $MoO_3$ ]

Norm. Mo (97.93) = [ Particles (1) of $Fe_2Mo_3O_{12}$ * $Mo_3$ mol weight (95.96 * 3 g) of $Fe_2Mo_3O_{12}$ + Particles (52) of $MoO_3$ * Mo mol weight (95.96 g) of $MoO_3$ ]
/ [ Particles (1) of $Fe_2Mo_3O_{12}$ * ($Fe_2$ and $Mo_3$ mol weight (55.85 * 2 g + 95.96 * 3 g) of $Fe_2Mo_3O_{12}$ + Particles (52) of $MoO_3$ * Mo mol weight (95.96 g) of $MoO_3$ ]

[FIG. 11]
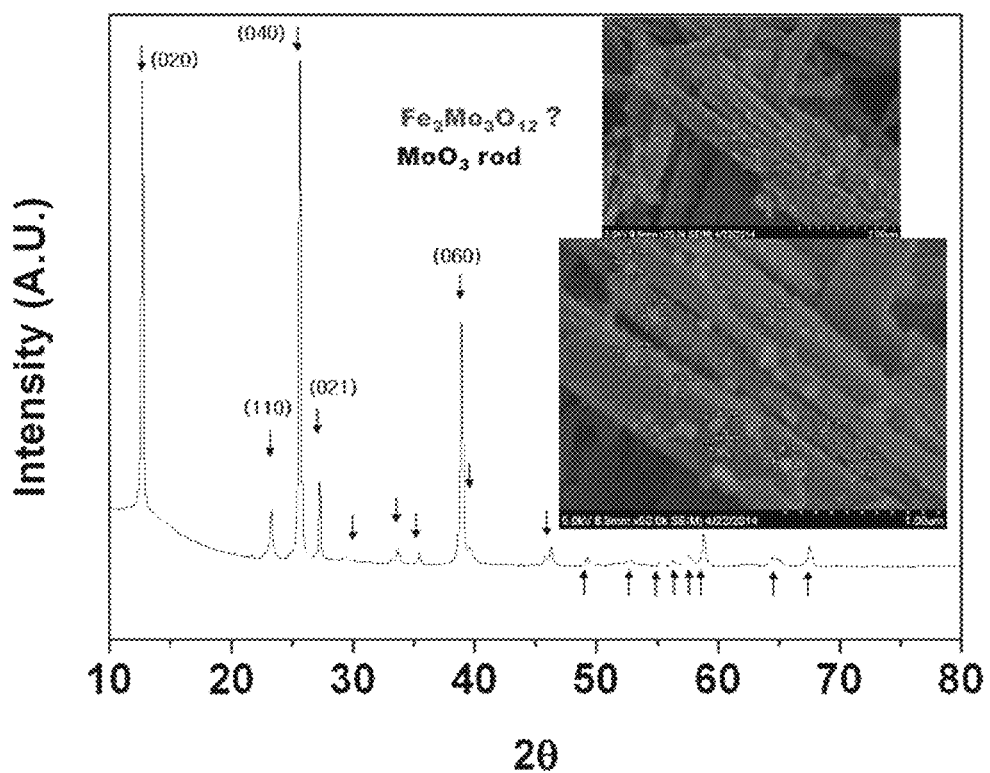

[Figure 12]

| EQUIPMENT | ICP | |
|---|---|---|
| RESULT | CONTENT(wt %) | |
| | Fe | Mo |
| Crystalline $Fe_2Mo_3O_{12}$ islands on $MoO_3$ | 5.7 | 59.9 |

| | ICP | |
|---|---|---|
| | Norm. Fe | Norm. Mo |
| Crystalline $Fe_2Mo_3O_{12}$ islands on $MoO_3$ | 8.69 | 91.31 |

Norm. Bi (8.84) = Particles (1) of $Fe_2Mo_3O_{12}$ * $Fe_2$ mol weight (55.85 * 2 g) of $Fe_2Mo_3O_{12}$
/
[ Particles (1) of $Fe_2Mo_3O_{12}$ * ($Fe_2$ and $Mo_3$ mol weight (55.85 * 2 g + 95.96 * 3 g) of $Fe_2Mo_3O_{12}$ + Particles (9) of $MoO_3$ * Mo mol weight (95.96 g) of $MoO_3$ ]

Norm. Mo (91.16) = [ Particles (1) of $Fe_2Mo_3O_{12}$ * $Mo_3$ mol weight (95.96 * 3 g) of $Fe_2Mo_3O_{12}$ + Particles (9) of $MoO_3$ * Mo mol weight (95.96 g) of $MoO_3$ ]
/
[ Particles (1) of $Fe_2Mo_3O_{12}$ * ($Fe_2$ and $Mo_3$ mol weight (55.85 * 2 g + 95.96 * 3 g) of $Fe_2Mo_3O_{12}$ + Particles (9) of $MoO_3$ * Mo mol weight (95.96 g) of $MoO_3$ ]

[FIG. 13]
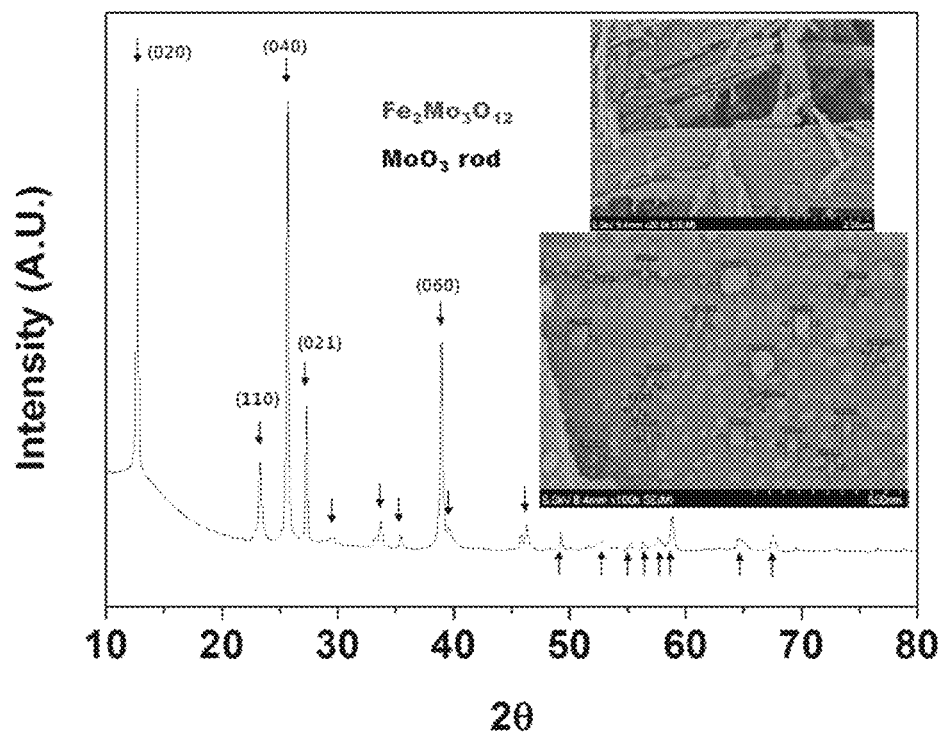

[FIG. 14]
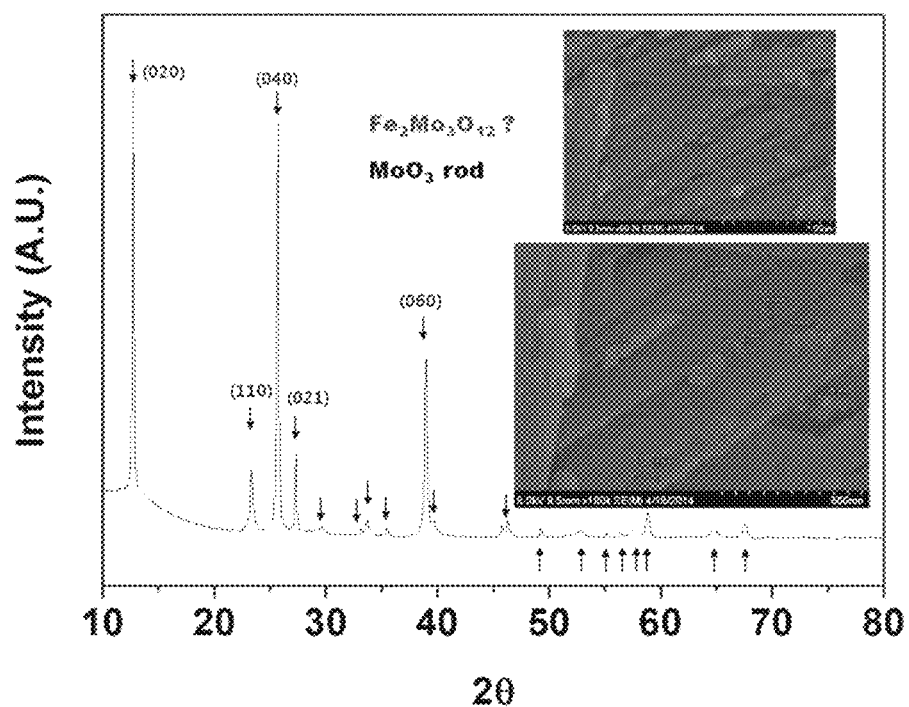

[FIG. 15]
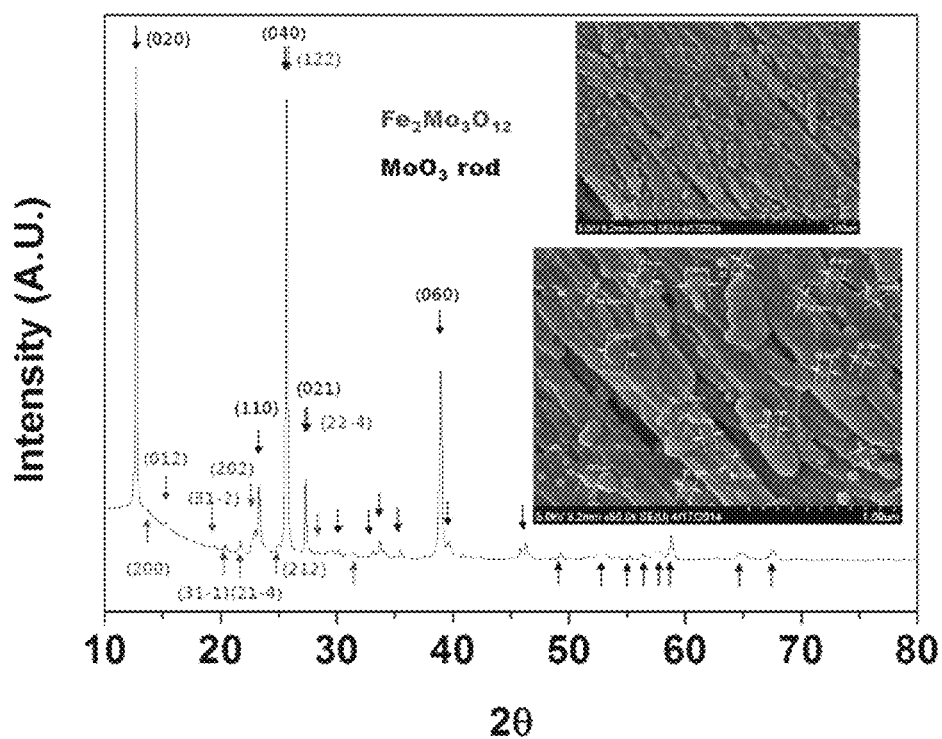

[FIG. 16]
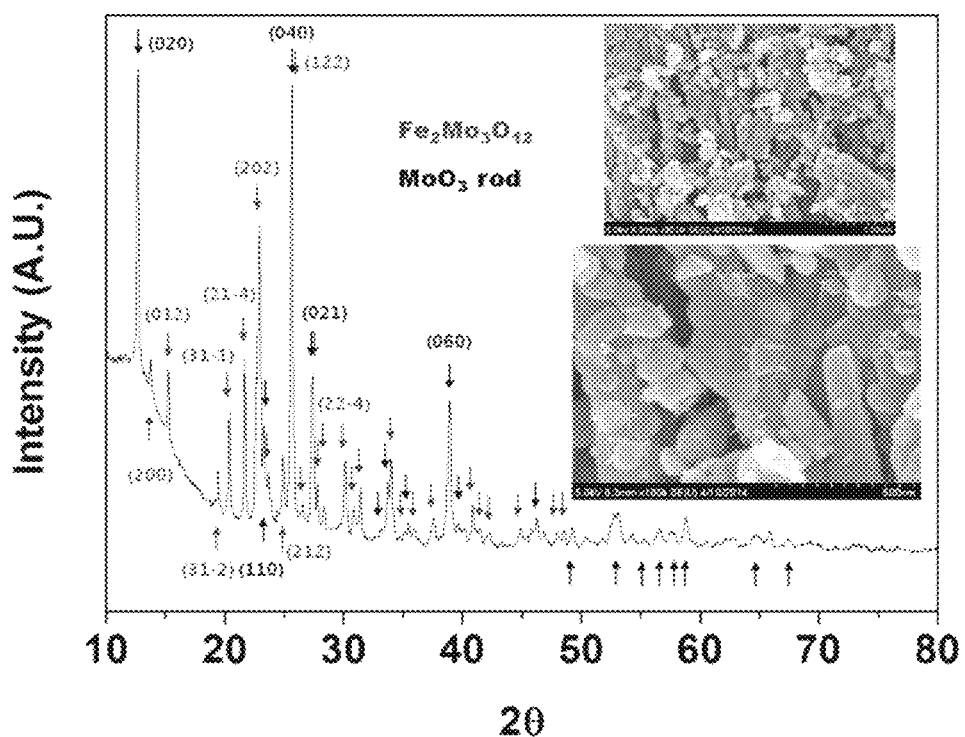

MOLYBDENUM OXIDE COMPOSITE AND PREPARATION METHOD THEREFOR

TECHNICAL FIELD

This application is a National Stage Entry of International Application No. PCT/KR2015/010326, filed on Sep. 30, 2015, and claims the benefit of and priority to Korean Application No. 10-2014-0132699, filed on Oct. 1, 2014, all of which are hereby incorporated by reference in their entirety for all purposes as if fully set forth herein.

The present invention relates to a molybdenum oxide composite and a preparation method thereof.

BACKGROUND ART

Metal molybdenum as silver-white hard transition metal has characteristics of having specific gravity of 10.22, very high melting point and boiling point of 2,610° C. and 5,560° C., respectively, good thermal conductivity, and low thermal expansion coefficient and thus has been frequently used as alloy elements for increasing hardness, strength, tensile strength, and wear resistance to high-temperature light-weight structural materials such as airplanes and missiles, high-temperature electrical materials such as filament supports and electrodes for electric furnaces, and special steel such as stainless steel, heat-resistant steel, and superalloy steel.

All around the world, about 70 to 80% of the used amount of the molybdenum metal is manufactured in a form of molybdenum oxide ($MoO_3$) briquettes or ferromolybdenum alloys to be used as alloy elements of steel and further, in a form of a molybdenum compound such as ammonium molybdate, sodium molybdate or molybdenum oxide powder, a considerable amount is also used in many petrochemical products such as catalysts, lubricants and pigments.

The molybdenum oxide may be used as a catalyst by forming a composite with metal molybdate and researches on the method of manufacturing the composite have been conducted and development of techniques to be performed in a better condition is required.

DETAILED DESCRIPTION OF THE INVENTION

Technical Problem

The present invention has been made in an effort to provide a molybdenum oxide composition and a preparation method thereof.

The present invention has been also made in an effort to provide a catalyst including the composite.

Technical Solution

An exemplary embodiment of the present invention provides a composite including rod-shaped molybdenum oxide and amorphous iron molybdate islands provided on the rod-shaped molybdenum oxide.

Another exemplary embodiment of the present invention provides a preparation method of the composite, including:

(a) preparing a mixed solution of an iron precursor and a solvent;

(b) preparing a mixed solution of rod-shaped molybdenum oxide and a solvent; and (c) mixing the solution (a) and the solution (b).

Yet another exemplary embodiment of the present invention provides a catalyst including the composite.

Advantageous Effects

According to the present invention, a composite including amorphous iron molybdate islands shows a smaller island size and a uniform distribution of islands compared with a conventional composite including crystalline islands, and thus has a higher specific surface area, thereby exhibiting excellent activity as a catalyst.

BRIEF DESCRIPTION OF DRAWINGS

FIG. 1 is a diagram illustrating an SEM analysis result of a composite including amorphous iron molybdate ($Fe_2Mo_3O_{12}$) islands provided on rod-shaped molybdenum oxide.

FIG. 2 is a diagram illustrating an SEM analysis result of measuring sizes of the amorphous iron molybdate ($Fe_2Mo_3O_{12}$) islands provided on rod-shaped molybdenum oxide.

FIG. 3 is a diagram illustrating an XRD analysis result of a composite including amorphous iron molybdate ($Fe_2Mo_3O_{12}$) islands provided on rod-shaped molybdenum oxide.

FIG. 4 is a diagram illustrating a TEM analysis result of a composite including amorphous iron molybdate ($Fe_2Mo_3O_{12}$) islands provided on rod-shaped molybdenum oxide.

FIG. 5 is a diagram illustrating an XPS analysis result of a composite including amorphous iron molybdate ($Fe_2Mo_3O_{12}$) islands provided on rod-shaped molybdenum oxide.

FIG. 6 is a diagram illustrating XRD and SEM analysis results of a composite including crystalline iron molybdate ($Fe_2Mo_3O_{12}$) islands provided on rod-shaped molybdenum oxide.

FIG. 7 is a diagram illustrating a TEM analysis result of a composite including crystalline iron molybdate ($Fe_2Mo_3O_{12}$) islands provided on rod-shaped molybdenum oxide, in which Point 1 represents the rod-shaped molybdenum oxide and Point 2 represents the crystalline iron molybdate ($Fe_2Mo_3O_{12}$) island.

FIGS. 8(*a*) and 8(*b*) are diagrams illustrating BET analysis results of a composite including amorphous iron molybdate islands provided on rod-shaped molybdenum oxide and FIG. 8(*c*) is a diagram illustrating a BET analysis result of a composite including crystalline iron molybdate islands provided on rod-shaped molybdenum oxide.

FIG. 9 is a diagram illustrating SEM and BET analysis results of iron molybdate powder.

FIG. 10 is a diagram illustrating an ICP analysis result and theoretical calculation of a composite including amorphous iron molybdate ($Fe_2Mo_3O_{12}$) islands provided on rod-shaped molybdenum oxide.

FIG. 11 is a diagram illustrating XRD and SEM analysis results of a composite including amorphous iron molybdate islands provided on rod-shaped molybdenum oxide by firing at 600° C. for 4 hrs.

FIG. 12 is a diagram illustrating an ICP analysis result and theoretical calculation of a composite including crystalline iron molybdate ($Fe_2Mo_3O_{12}$) islands provided on rod-shaped molybdenum oxide.

FIG. 13 is a diagram illustrating XRD and SEM analysis results of a composite including amorphous iron molybdate islands provided on rod-shaped molybdenum oxide by firing at 500° C. for 12 hrs.

FIG. 14 is a diagram illustrating XRD and SEM analysis results of a composite prepared in Comparative Example 2 of the present invention.

FIG. 15 is a diagram illustrating XRD and SEM analysis results of a composite prepared in Comparative Example 3 of the present invention.

FIG. 16 is a diagram illustrating XRD and SEM analysis results of a composite prepared in Comparative Example 4 of the present invention.

BEST MODE

The advantages and features of the present invention, and a method of accomplishing these will become obvious with reference to embodiments to be described below in detail along with the accompanying drawings. However, the present invention is not limited to the following exemplary embodiments but may be implemented in various different forms. The exemplary embodiments are provided only to complete disclosure of the application and to fully provide a person having ordinary skill in the art to which the present invention pertains with the category of the invention, and the present invention will be defined by the appended claims.

Unless otherwise defined, all terms including technical and scientific terms used in the present specification may be used as the meaning which may be commonly understood by the person with ordinary skill in the art, to which this application pertains. It will be further understood that terms defined in commonly used dictionaries should not be interpreted in an idealized or excessive sense unless expressly and specifically defined.

Hereinafter, the present invention will be described in detail.

An exemplary embodiment of the present invention provides a composite including rod-shaped molybdenum oxide and amorphous iron molybdate islands provided on the rod-shaped molybdenum oxide.

As described above, currently, the molybdenum oxide has been used as catalysts of various reactions and particularly, has been frequently used as catalysts of partial oxidation reactions.

Currently, as the catalyst, researches for an activity increase of molybdenum oxide have been conducted, and researches such as preparing metal molybdenum by adding metal or preparing a composite of metal and molybdenum oxide have been conducted.

Among them, a composite of metal and molybdenum oxide has excellent activity or selectivity as a catalyst of partial oxidation reaction compared with pure rod-shaped molybdenum oxide or pure metal molybdenum.

Accordingly, there are a lot of researches for a composite of iron and molybdenum oxide among the composites, and a lot of researches for a structure capable of having a higher specific surface area have been conducted. However, even though the structures synthesized by the above researches ensure a high specific surface area, there is a problem in that the structures are easily brittle and there is a disadvantage that preservation and handling after preparation are difficult.

To solve the problems, a composite in which metal islands are formed on the rod-shaped molybdenum oxide has been developed, but in the related art, the island provided on the composite is present only in the crystalline form.

However, the inventors studied for the purpose to increase the activity of the catalyst and prepared a composite including rod-shaped molybdenum oxide and amorphous iron molybdate ($Fe_2Mo_3O_{12}$) islands provided on the rod-shaped molybdenum oxide of the present invention.

In this specification, amorphous is a solid material and has a uniform composition, but means a state where atomic arrangement is disordered like a liquid and is not in a regular lattice form.

However, in this specification, in the amorphous, the iron molybdate islands need not to be 100% amorphous and the iron molybdate islands provided on the rod-shaped molybdenum oxide according to the exemplary embodiment of the present invention include 50% or more of an amorphous form and the rest of a crystalline form.

In the composite according to the exemplary embodiment of the present invention, the iron molybdate ($Fe_2Mo_3O_{12}$) islands provided on the rod-shaped molybdenum oxide are not crystalline but amorphous. That is, the composite is not a solid form having a regular atomic arrangement in the island like an existing crystalline form, but is a solid material and has a disordered form like a liquid without having a regularity of the atomic arrangement in one island.

A size of the amorphous island according to the exemplary embodiment of the present invention has a smaller uniform distribution than the existing crystalline island. Accordingly, the amorphous island has a higher specific surface area than the existing composite and contributes to an activity increase of the catalyst.

In this specification, the molybdenum oxide is an oxidized form of molybdenum (Mo), has various structures, and includes $MoO_3$.

In this specification, the rod shape may be used as a general geometric meaning and includes an elongated form in which a size of one axis is larger than that of the other axis.

In this specification, hereinafter, the longest particle diameter of the rod-shaped molybdenum oxide is referred to as a length and a shortest particle diameter is referred to as a line width.

According to an exemplary embodiment of the present invention, the length of the rod-shaped molybdenum oxide is in a range of 500 nm to 20 μm, preferably a range of 500 nm to 4 μm, and more preferably a range of 500 nm to 2.5 μm.

According to an exemplary embodiment of the present invention, the line width of the rod-shaped molybdenum oxide is in a range of 100 nm to 1.5 μm, preferably a range of 100 nm to 1 μm, and more preferably a range of 100 nm to 300 nm.

According to an exemplary embodiment of the present invention, the line width of the rod-shaped molybdenum oxide is 300 nm or less and the most of rod-shaped molybdenum oxide has a line width of 250 nm.

According to an exemplary embodiment of the present invention, when the length and the line width of the rod-shaped molybdenum oxide are in the ranges, a high specific surface area may be ensured, and the catalyst including the rod-shaped molybdenum oxide having the high specific surface area has an excellent activity by ensuring a higher contact area than that of an existing material having low specific surface area.

According to an exemplary embodiment of the present invention, a ratio of the line width to the length of the rod-shaped molybdenum oxide is in a range of 5:1 to 13:1 and more preferably 6:1 to 10:1. As such, in the case of the rod-shaped molybdenum oxide having the ratio range of the line width to the length, a greater number of molybdenum oxides than the same weight than a flat molybdenum oxide may be ensured to increase a specific surface area.

According to an exemplary embodiment of the present invention, the island is not particularly limited as a material containing iron and molybdenum, but may include a material represented by $Fe_2Mo_3O_{12}$. Alternatively, the island according to an exemplary embodiment of the present invention may be a material represented by $Fe_2Mo_3O_{12}$.

According to an exemplary embodiment of the present invention, in the composite, the content of the island is 10 wt % or less, preferably 7 wt % or more and 10 wt % or less, and more preferably 7.32 wt % or more and 9.76 wt % or less based on the overall complex.

According to an exemplary embodiment of the present invention, the composite is a structure with 20 to 100 islands per one rod-shaped molybdenum oxide.

According to an exemplary embodiment of the present invention, the size of the island is in a range of 10 nm to 150 nm or 10 nm to 120 nm, and in the preparation process of the composite to be described below, the size of the island may vary according to a firing temperature and a firing time.

Further, according to an exemplary embodiment of the present invention, the size of the island is preferably in a range of 10 nm to 50 nm and shows a smaller uniform distribution compared to the existing crystalline island.

According to an exemplary embodiment of the present invention, most of amorphous islands are present in a rectangular form, and the size of one island is measured based on the shortest length and the size of approximately 50 islands is measured based on an SEM image of FIG. 1.

In Experimental Example of the present invention, an additional SEM analysis result of measuring the size of the amorphous iron molybdate island is illustrated in FIG. 2 and in FIG. 2(b), it was verified that the size of the island is in a range of 10 nm to 50 nm like the SEM analysis result of FIG. 1.

According to an exemplary embodiment of the present invention, a ratio of particle numbers configuring the molybdenum oxides and the islands in the composite is in a range of 30:1 to 60:1, preferably 38:1 to 52:1, and more preferably 50:1 to 52:1.

According to an exemplary embodiment of the present invention, a mass ratio of Fe to Mo in the composite is in a range of 1:30 to 1:60, preferably 1:30 to 1:50, and more preferably 1:35 to 1:47. In Experimental Example of the present invention, a mass ratio of Mo to Fe in the composite of the iron molybdenum with the amorphous iron molybdenum islands on the rod-shaped molybdenum oxide and the rod-shaped molybdenum oxide is shown by an ICP analysis result and a theoretical calculation.

According to an exemplary embodiment of the present invention, at a point where a mass ratio of Mo to Fe in the composite is 1:35, in the case of increasing the mass of Mo, the iron molybdate island having a size of 50 nm or more is prevented from being mainly formed and amorphous iron molybdate other than crystalline may be formed.

According to an exemplary embodiment of the present invention, at a point where a mass ratio of Mo to Fe in the composite is 1:47, in the case where the content of Mo is small, the number of iron molybdate islands having a size of 20 nm to 50 nm on the rod-shaped molybdenum oxide is sufficiently formed and many islands having 10 nm or less are prevented from being distributed.

In Experimental Example of the present invention, it is verified that when the mass ratio of Mo to Fe in the composite is 3:31, the iron molybdate islands having a size of 80 nm to 200 nm are mainly distributed and the islands are crystalline. A result of showing the mass ratio of Mo to Fe in the composite through an ICP analysis result and theoretical calculation is illustrated in FIG. 12.

According to an exemplary embodiment of the present invention, the composite has a specific surface area in a range of 8 $m^2/g$ to 12 $m^2/g$ and more preferably in a range of 8.47 $m^2/g$ to 11.31 $m^2/g$.

According to an exemplary embodiment of the present invention, when the specific surface area is 8 $m^2/g$ or more, the size of the island formed on the rod-shaped molybdenum oxide is increased to prevent the island from being formed as crystalline. That is, when the specific surface area of the composite is in a range of 8 $m^2/g$ to 12 $m^2/g$, the island is amorphous and the size of the island may have 50 nm or less.

For example, in Experimental Example of the present invention, the specific surface area of the composite including the amorphous iron molybdate islands provided on the rod-shaped molybdenum oxide is 11.31 $m^2/g$ and the experimental result is illustrated in FIG. 8(b).

The composite including the amorphous iron molybdate islands according to an exemplary embodiment of the present invention has a higher specific surface area than pure $Fe_2Mo_3O_{12}$ powder used as a catalyst of existing partial oxidation reaction.

For example, in Experimental Example of the present invention, the composite including the amorphous islands has a higher specific surface area than 7.931 $m^2/g$ which is a specific surface area of the composite including the existing crystalline islands and the experimental result is illustrated in FIG. 8.

Further, in Experimental Example of the present invention, the composite has 8.47 to 11.31 $m^2/g$ which is a higher specific surface area than 7.06 $m^2/g$ which is a specific surface area of the existing pure iron molybdate ($Fe_2Mo_3O_{12}$) powder and the experimental result is illustrated in FIGS. 8 and 9.

Another exemplary embodiment of the present invention provides a preparation method of the composite, including:

(a) preparing a mixed solution of an iron precursor and a solvent;

(b) preparing a mixed solution of rod-shaped molybdenum oxide and a solvent; and (c) mixing the solution (a) and the solution (b).

According to an exemplary embodiment of the present invention, preparation methods of the iron molybdenum and the rod-shaped molybdenum oxide composite are performed by gram scales.

The preparation method of the composite including the existing crystalline islands is performed by milligram scale and in the case of being performed by the milligram scale, only the crystalline islands are formed.

As described above, compared with the composite with the existing crystalline islands, the composite with the amorphous islands according to the present invention includes islands having smaller sizes and a uniform distribution. Accordingly, the composite according to the exemplary embodiment of the present invention has a higher specific surface area and an advantage of having high activity when being used as the catalyst of the partial oxidation reaction.

According to an exemplary embodiment of the present invention, an iron precursor in step (a) is various materials including iron and an unlimited example of the iron precursor is a material represented by $Fe(NO_3)_3 \cdot 9H_2O$, $Fe(NO_3)_3$, $Fe(OH)_3$ or $Fe_2O_3$ and more preferably $Fe(NO_3)_3 \cdot 9H_2O$.

According to an exemplary embodiment of the present invention, as the solvent used in steps (a) and (b), a material having an OH functional group such as alcohol and polyol may be used and preferably, water is used.

Further, according to an exemplary embodiment of the present invention, as the solvent used in steps (a) and (b), a material having an OH functional group such as alcohol and polyol and a small amount of water may be used.

According to an exemplary embodiment of the present invention, the material having the OH functional group is a compound having one or more OH groups and as a preferable example, there is water, ethanol, or the like.

According to an exemplary embodiment of the present invention, step (a) includes adding a solvent to the iron precursor or adding the iron precursor to the solvent.

According to an exemplary embodiment of the present invention, step (a) includes stirring a mixed solution of the iron precursor and water.

According to an exemplary embodiment of the present invention, step (a) may be performed at room temperature and preferably, may be performed in a range of 20° C. to 30° C.

According to an exemplary embodiment of the present invention, the rod-shaped molybdenum oxide used in step (b) may be prepared by reacting molybdenum oxide powder with a hydrogen peroxide solution.

According to an exemplary embodiment of the present invention, as the hydrogen peroxide solution, a solution at a concentration of 10 to 50 wt % of hydrogen peroxide may be used. The hydrogen peroxide solution may include a solvent and as the solvent, a generally used material may be used and as an example, water may be used.

According to an exemplary embodiment of the present invention, the molybdenum oxide powder includes various forms and may use commercial powder.

According to an exemplary embodiment of the present invention, the molybdenum oxide powder includes a plate-shaped form.

According to an exemplary embodiment of the present invention, the molybdenum oxide powder may be used to have sizes of length and width of several μm scales.

According to an exemplary embodiment of the present invention, the preparing of the rod-shaped molybdenum oxide includes mixing the hydrogen peroxide solution and the molybdenum oxide powder, and the mixing of the hydrogen peroxide solution and the molybdenum oxide powder includes adding the molybdenum oxide powder to the hydrogen peroxide solution or adding the hydrogen peroxide solution to the molybdenum oxide powder.

According to an exemplary embodiment of the present invention, the preparing of the rod-shaped molybdenum oxide includes preparing the rod-shaped molybdenum oxide through a hydrothermal synthesis method by mixing the hydrogen peroxide solution and the molybdenum oxide powder.

According to an exemplary embodiment of the present invention, the preparing of the rod-shaped molybdenum oxide includes stirring and heating the mixed solution of the hydrogen peroxide solution and the molybdenum oxide powder.

In this specification, the hydrothermal synthesis method is a method of synthesizing a material using water as one of liquid synthesis methods.

According to yet another exemplary embodiment of the present invention, the preparing of the rod-shaped molybdenum oxide may include 1) forming $MoO_2(OH)(OOH)$ by reacting the hydrogen peroxide solution and the molybdenum oxide powder and 2) forming the rod-shaped molybdenum oxide from the $MoO_2(OH)(OOH)$ through a hydrothermal synthesis method.

According to an exemplary embodiment of the present invention, step 1) is performed at a temperature of 95° C. or less to form $MoO_2(OH)(OOH)$ under a low pressure condition. According to an exemplary embodiment of the present invention, step 1) includes isolating $MoO_2(OH)(OOH)$ as a reaction product.

According to an exemplary embodiment of the present invention, the preparing of the rod-shaped molybdenum oxide includes drying while or after isolating $MoO_2(OH)(OOH)$.

According to yet another exemplary embodiment of the present invention, the drying may include drying in a vacuum oven and $MoO_2(OH)(OOH)$ powder may be obtained.

According to an exemplary embodiment of the present invention, step (b) includes adding a solvent to the rod-shape molybdenum oxide or adding the rod-shape molybdenum oxide to the solvent.

According to an exemplary embodiment of the present invention, step (b) includes heating a mixed solution of the rod-shape molybdenum oxide and water.

According to an exemplary embodiment of the present invention, in step (b), the heating includes heating from room temperature to a range of 40° C. to 50° C. and the temperature means a temperature of the solution of the rod-shape molybdenum oxide.

According to an exemplary embodiment of the present invention, when the temperature is 40° C. or more, the dissociation rate of the surface of the rod-shaped molybdenum oxide is sufficiently ensured, so that the iron precursor has the effect of performing the reaction on the surface of the rod-shaped molybdenum oxide, and when the temperature is 50° C. or less, the dissociation of the surface of the rod-shaped molybdenum oxide is accelerated to prevent the shape of the rod-shaped molybdenum oxide from being deformed.

According to an exemplary embodiment of the present invention, step (b) includes stirring while or after heating the mixed solution of the rod-shape molybdenum oxide and water.

According to an exemplary embodiment of the present invention, step (c) includes dropping the solution of (a) in the solution (b) at a constant speed.

According to an exemplary embodiment of the present invention, in step (c), a speed of dropping the solution of (a) in the solution of (b) is in a range of 4 ml/min to 5 ml/min.

According to an exemplary embodiment of the present invention, when the dropping speed is in a range of 4 ml/min to 5 ml/min, the surface of the rod-shaped molybdenum oxide is appropriately dissociated to have an effect of activating uniform adsorption on the surface of the rod-shaped molybdenum oxide of $Fe(OH)_3$ formed from the iron precursor and water.

According to an exemplary embodiment of the present invention, step (c) includes stirring a mixed solution of the solution (a) and the solution of (b).

According to an exemplary embodiment of the present invention, after step (c), isolating the composite generated through step (c) is included.

According to an exemplary embodiment of the present invention, the isolating may be performed through a centrifuge.

According to an exemplary embodiment of the present invention, while or after the isolating, drying is included.

According to an exemplary embodiment of the present invention, the drying may be performed through a vacuum oven.

According to an exemplary embodiment of the present invention, after step (c), (d) firing is included.

According to an exemplary embodiment of the present invention, the (d) firing step may be performed in a range of 500° C. to 700° C. or 500° C. to 650° C., preferably 500° C. to 600° C. and preferably, the firing is performed in a temperature range of 500° C. to 550° C. and a range of 3 hrs to 5 hrs.

According to an exemplary embodiment of the present invention, the iron precursor solution forms a material represented by $Fe(OH)_3$ through hydrolysis in step (a). That is, the hydrolysis process of the iron precursor solution of (a) may be performed by Chemical Formula such as $Fe(NO_3)_3 + 3H_2O \rightarrow Fe(OH)_3 + 3HNO_3$.

According to an exemplary embodiment of the present invention, step (c) includes accumulating a material containing iron (Fe) such as $Fe(OH)_3$ on the surface of the rod-shaped molybdenum oxide.

According to an exemplary embodiment of the present invention, step (d) includes (d-1) changing a material represented by $Fe(OH)_3$ accumulated on the surface of the rod-shaped molybdenum oxide into a material represented by $Fe_2O_3$ and (d-2) changing the material represented by $Fe_2O_3$ into a material represented by $Fe_2Mo_3O_{12}$.

According to an exemplary embodiment of the present invention, step (d) includes forming the material represented by $Fe_2Mo_3O_{12}$ by reacting iron oxide with the surface the rod-shaped molybdenum oxide and the reaction may be performed by Chemical Formula such as $Fe_2O_3 + 3MoO_3 \rightarrow Fe_2Mo_3O_{12}$.

According to an exemplary embodiment of the present invention, $Fe_2Mo_3O_{12}$ particles formed through step (d) are gradually accumulated to form amorphous islands having sizes of 10 nm to 120 nm and more preferably form amorphous iron molybdenum islands having sizes of 10 nm to 50 nm.

Yet another exemplary embodiment of the present invention provides a catalyst including the composite of the iron molybdenum and the rod-shaped molybdenum oxide.

According to an exemplary embodiment of the present invention, the catalyst participates in the chemical reaction to change a reaction speed, but the catalyst itself is a material remaining as it is before and after the reaction.

That is, when the chemical reaction proceeds, the reaction material needs to pass through an activated state, and since the activated state is a higher energy state than the reaction material or the generation material, the reaction material needs to have sufficient energy so that the reaction occurs. The catalyst allows the reaction of the reaction material to occur through a lower or higher path than the activated energy.

According to an exemplary embodiment of the present invention, the composite of the iron molybdenum and the rod-shaped molybdenum oxide is used as the catalyst to have an effect of improving reactivity by increasing a reaction area.

According to an exemplary embodiment of the present invention, the rod-shaped molybdenum oxide may be used as a catalyst of various partial oxidation reactions and as an example, may be used as a catalyst of partial oxidation reaction generating 1,3-butadiene from 1-butene.

Hereinafter, the present invention will be described in more detail through Examples. However, Examples according to the present invention may be modified in various different forms and the scope of the present invention is not limited to the following Examples. Examples of the present invention will be provided for more completely describing the present invention to those skilled in the art.

Preparation of Composite

Examples

Example 1

1.6 g of $Fe(NO_3)_3$ $9H_2O$ was added in 100 ml of water and stirred at room temperature. Meanwhile, 1.2 g of rod-shaped molybdenum oxide was added in 50 ml of water and stirred by heating to a temperature of 50° C. A iron precursor ($Fe(NO_3)_3$ $9H_2O$) solution was dropped into the rod-shaped molybdenum oxide solution at a speed of 4 to 5 ml/min and then stirred and maintained for 2 hrs. Thereafter, a rod-shaped molybdenum oxide sample inserted with an iron precursor was isolated by using a centrifuge and dried in a vacuum oven of 80° C. The dried sample was fired at a temperature of 500° C. for 4 hrs in the air.

The islands of the prepared composite were formed on the rod-shaped molybdenum oxide to have a uniform distribution and have sizes of 10 nm to 50 nm. Further, the island was amorphous $Fe_2Mo_3O_{12}$.

The $Fe_2Mo_3O_{12}$ island particles and the rod-shaped molybdenum oxide particles had a particle number ratio of 1:38 to 1:52 and a mass distribution of the islands for the composite had 7.32 wt % to 9.76 wt %.

Further, it was verified that a mass ratio of Mo to Fe was constituted by 1:35 to 1:47 and a specific surface area of 8.47 $m^2/g$ to 11.31 $m^2/g$ of the composite prepared in Example 1 had a higher specific surface area than the composite (7.931 $m^2/g$) formed with crystalline $Fe_2Mo_3O_{12}$ islands on the $Fe_2Mo_3O_{12}$ powder (7.06 $m^2/g$) or the rod-shaped molybdenum oxide, and the result was illustrated in FIGS. 8 and 9.

Particularly, the SEM analysis result of the composite prepared in Example 1 was illustrated in FIGS. 1 and 2 and an XRD analysis result of the composite including a rod-shaped molybdenum oxide and amorphous $Fe_2Mo_3O_{12}$ islands provided on the rod-shaped molybdenum oxide was illustrated in FIG. 3, and as the result, a crystalline phase of only $MoO_3$ was detected.

In FIG. 4, in order to determine a composition of the islands provided on the rod-shaped molybdenum oxide, a TEM analysis result was shown and through the analysis result, Fe components were detected only in the islands.

Similarly, in FIG. 5, an XPS analysis result for determining a composition of the islands provided on the rod-shaped molybdenum oxide was shown. In the XPS analysis result, it was verified that Fe and Mo oxidation numbers of the amorphous islands ($Fe_2Mo_3O_{12}$) according to the present invention were present as $3^+$ and $6^+$, respectively, and the oxidation numbers were constituted by the same oxidation number as the crystalline islands ($Fe_2Mo_3O_{12}$). Further, in the case of the amorphous islands ($Fe_2Mo_3O_{12}$) according to the present invention, the oxidation number of some Fe was detected as $2^+$, and it was determined that the reason was that irregularity of Fe structure due to amorphous was increased. As a result, it was established that the islands formed on the molybdenum oxide according to the present invention were amorphous.

Example 2

Except for performing firing at 600° C. for 4 hrs, a composite was prepared by the same method as Example 1 described above.

In the prepared composite, the island provided on the rod-shaped molybdenum oxide had a size of 30 nm to 120 nm, the particle size of the island was increased compared to Example 1 described above, and it was found that uniform distribution of the islands was slightly deteriorated. However, in spite of the phenomenon, the island still showed an amorphous phase and was illustrated in FIG. 11.

Example 3

Except for performing firing at 500° C. for 12 hrs, a composite was prepared by the same method as Example 1 described above.

In the prepared composite, the island provided on the rod-shaped molybdenum oxide had a size of 25 nm to 110 nm, the particle size of the island was increased compared to Example 1 described above, and it was found that uniform distribution of the islands was slightly deteriorated. However, in spite of the phenomenon, the island still showed an amorphous phase and was illustrated in FIG. 13.

As a result, even though a firing temperate and a firing time were increased, it was verified that the phases of the islands on the rod-shaped molybdenum oxide were maintained as amorphous and it was verified that the content of the islands for the entire composite through Examples 1 to 3 described above was in a range of 7.32 wt % to 9.76 wt %.

Comparative Example 1

300 mg of $Fe(NO_3)_3$ $9H_2O$ was added in 50 ml of water and stirred at room temperature. Meanwhile, 225 mg of rod-shaped molybdenum oxide was added in 50 ml of water and stirred by heating to a temperature of 50° C. A iron precursor $(Fe(NO_3)_3$ $9H_2O)$ solution was dropped into the rod-shaped molybdenum oxide solution at a speed of 4 to 5 ml/min and then stirred and maintained for 2 hrs. Thereafter, a rod-shaped molybdenum oxide sample inserted with an iron precursor was isolated by using a centrifuge and dried in a vacuum oven of 80° C. The dried sample was fired at a temperature of 500° C. for 4 hrs in the air.

In FIG. 6, XRD and SEM analyst results of a composite including a rod-shaped molybdenum oxide and crystalline $Fe_2Mo_3O_{12}$ islands provided on the rod-shaped molybdenum oxide were illustrated.

In FIG. 7, a TEM analyst result of a composite including a rod-shaped molybdenum oxide and crystalline $Fe_2Mo_3O_{12}$ islands provided on the rod-shaped molybdenum oxide was illustrated. Point 1 of FIG. 7 represented the rod-shaped molybdenum oxide and Point 2 represented the crystalline $Fe_2Mo_3O_{12}$ islands.

In the prepared composite, it was verified that the island provided on the rod-shaped molybdenum oxide had a size of 80 nm to 200 nm and the phase of the island was crystalline.

Further, it was verified that a ratio of the particle number configuring the rod-shaped molybdenum oxide to the particle number configuring the islands was in a range of 1:7 to 1:9 and the content of the islands for the entire composite was in a range of 31.3 wt % to 37 wt %. Further, a mass ratio of Fe and Mo was in a range of 1:9 to 3:31 and illustrated in FIGS. 6, 7, and 12, and a specific surface area of the composite prepared in Comparative Example 1 was illustrated in FIG. 8 and was 7.931 $m^2/g$.

Comparative Example 2

0.4 g of $Fe(NO_3)_3$ $9H_2O$ was added in 50 ml of water and stirred at room temperature. Meanwhile, 1.2 g of rod-shaped molybdenum oxide was added in 50 ml of water and stirred by heating to a temperature of 50° C. A iron precursor $(Fe(NO_3)_3$ $9H_2O)$ solution was dropped into the rod-shaped molybdenum oxide solution at a speed of 4 to 5 ml/min and then stirred and maintained for 2 hrs. Thereafter, an amount of the iron precursors input by removing water as the solvent by using a liquid evaporator was fully impregnated on the rod-shaped molybdenum oxide. In a centrifuge method, only the amount of some iron precursors was accumulated on the rod-shaped molybdenum oxide and thus it was difficult to increase the amount of the iron precursors on the rod-shaped molybdenum oxide. As a result, a sample from which the solvent was removed was dried in a 80° C. vacuum oven by using a liquid evaporator. The dried sample was fired at a temperature condition of 500° C. for 4 hrs in the air.

Comparative Example 3

Except for performing firing at 550° C., a composite was prepared by the same method as Comparative Example 2 described above.

In the composite prepared in Comparative Examples 2 and 3 described above, the islands were distributed on another island as well as the rod-shaped molybdenum oxide and did not have a uniform distribution, and it was verified that in Comparative Example 2, the particle size of the island was in a range of 20 nm to 150 nm and in Comparative Example 3, the particle size of the island was slightly wide in a range of 50 nm to 200 nm.

It was verified that the phases of the islands were amorphous in Comparative Example 2 and crystalline in Comparative Example 3 and the phases were illustrated in FIGS. 14 and 15, respectively. Further, the content of islands for the entire composite in Comparative Examples 2 and 3 was in a range of 20 wt % to 25 wt %.

As a result, it was verified that the phases of the islands was partially changed from amorphous to crystalline by increasing a firing temperature and a firing time and it was verified that the content of islands was only 10 wt % or less so that the phase of the island was maintained as amorphous regardless of a firing temperature and a firing time.

Comparative Example 4

1.6 g of $Fe(NO_3)_3$ $9H_2O$ was added in 100 ml of water and stirred at room temperature. Meanwhile, 1.2 g of rod-shaped molybdenum oxide was added in 50 ml of water and stirred by heating to a temperature of 50° C. An iron precursor $(Fe(NO_3)_3$ $9H_2O)$ solution was dropped into the rod-shaped molybdenum oxide solution at a speed of 4 to 5 ml/min and then stirred and maintained for 2 hrs. Thereafter, an amount of the iron precursor input by removing a solvent $(H_2O)$ by using a liquid evaporator was fully impregnated on the rod-shaped molybdenum oxide. The sample from which the solvent was removed was dried in an 80° C. vacuum oven and the dried sample was fired at a temperature of 500° C. for 4 hrs in the air.

In the prepared composite, the islands on the rod-shaped molybdenum oxide were present on another island as well as the rod-shaped molybdenum oxide and were not distributed with a uniform size, and had sizes of 50 nm to 200 nm. Further, the island was crystalline $Fe_2Mo_3O_{12}$ and illustrated in FIG. 16 and the mass distribution of the composite islands was about 75.0 wt % to 80.0 wt %.

Accordingly, through Comparative Example 4, it has been found that the content of $Fe_2Mo_3O_{12}$ islands played an important role so that the island phase was amorphous.

Experimental Example 1

The composite including a rod-shaped molybdenum oxide and the amorphous iron molybdate islands provided on the rod-shaped molybdenum oxide prepared according to the Examples described above was used in a reaction of preparing 1,3-butadiene from 1-butene as a catalyst of the partial oxidation reaction and the experimental process was as follows in detail.

3 g of composite powder including a rod-shaped molybdenum oxide and amorphous iron molybdate islands provided on the rod-shaped molybdenum oxide prepared in Examples described above made a pellet by using a hydraulic machine and a pelletizer and the pellet was cleaved in sieves having a size of 1,180 μm and a size of 600 μm to prepare a sample having a size of 600 μm to 1,180 μm.

1.5 g of the sample was added in a high through-put system (HTS) reactor and heated to 400° C. from room temperature under a gas condition of $N_2$: 28.6 sccm and $O_2$: 7.14 sccm and then pre-treated for 1 hr. The sample was cooled to 320° C. and maintained for 30 minutes by turning on steam: 10 sccm. The sample was reacted for 30 minutes under a gas condition of $N_2$: 20 sccm, $O_2$: 2.5 sccm, steam: 6.67 sccm, and 1-butene: 1.67 sccm and a detection reaction was performed through gas chromatography.

It was shown that the composition of the amorphous iron molybdate islands on the rod-shaped molybdenum oxide had a conversion rate of 47.6%, BD (1,3-butadiene) selectivity of 9.16%, and BD yield of 4.36%, and it was shown that except for yield (a conversion rate of 39.1%, BD selectivity of 8.51%, and BD yield of 3.32%) of the rod-shaped molybdenum oxide itself, the BD yield of the amorphous iron molybdate islands was 1.04%.

Through ICP analysis illustrated in FIG. 10, it was shown that a ratio of the amorphous iron molybdate islands of the composite was constituted by 7.32 wt % and reaction efficiency of the amorphous iron molybdate islands was 1.04%/0.0732=14.2%.

It was shown that reaction efficiency was higher than powder (crystalline $Fe_2Mo_3O_{12}$ powder and BD yield of 6.36%) constituted by 100% crystalline iron molybdate in Comparative Experimental Example to be described below.

Comparative Experimental Example

Except for using powder constituted by 100% crystalline iron molybdate as a catalyst, Comparative Experimental Example was experimented by the same method as Experimental Example 1 described above.

In this case, the powder constituted by the 100% crystalline iron molybdate had a conversion rate of 49.9%, BD selectivity of 12.74%, and BD yield of 6.36%.

The invention claimed is:

1. A composite including a rod-shaped molybdenum oxide and amorphous iron molybdate islands provided on the rod-shaped molybdenum oxide,
    wherein a ratio of respective particle numbers constituting the rod-shaped molybdenum oxide and the islands in the composite is in a range of 30:1 to 60:1,
    wherein a mass ratio of molybdenum (Mo) to iron (Fe) included in the amorphous iron molybdate islands on the rod-shaped molybdenum oxide in the composite is in a range of 1:35 to 1:47, and
    wherein the amorphous iron molybdate islands comprises 50% or more of an amorphous form and a remainder of a crystalline form.

2. The composite of claim 1, wherein the iron molybdate island includes a material represented by $Fe_2Mo_3O_{12}$.

3. The composite of claim 1, wherein the content of islands is 10 wt % or less with respect to the entire composite.

4. The composite of claim 1, wherein 20 to 100 islands per one rod-shaped molybdenum oxide are included.

5. The composite of claim 1, wherein the size of the island is in a range of 10 nm to 50 nm.

6. The composite of claim 1, wherein a specific surface area of the composite is in a range of 8 $m^2$/g to 12 $m^2$/g.

7. A preparation method of the composite of claim 1, the method comprising:
    (a) preparing a mixed solution of an iron precursor and a solvent;
    (b) preparing a mixed solution of rod-shaped molybdenum oxide and a solvent; and
    (c) mixing the solution of (a) and the solution of (b),
    wherein step (b) includes heating a mixed solution of the rod-shaped molybdenum oxide and a solvent, and
    wherein the heating is performed from room temperature to a range of 40° C. to 50° C.

8. The preparation method of claim 7, wherein the preparation method of the composite is performed by a gram scale.

9. The preparation method of claim 7, wherein the iron precursor is a material represented by $Fe(NO_3)_3$ $9H_2O$, $Fe(NO_3)_3$, $Fe(OH)_3$ or $Fe_2O_3$.

10. The preparation method of claim 7, wherein step (a) includes stirring a mixed solution of the iron precursor and a solvent.

11. The preparation method of claim 7, wherein step (b) includes stirring while or after heating the mixed solution of the rod-shaped molybdenum oxide and the solvent.

12. The preparation method of claim 7, wherein step (c) includes dropping the solution of (a) in the solution of (b) at a constant speed.

13. The preparation method of claim 7, further comprising:
    isolating the composite of the iron molybdenum and the rod-shaped molybdenum oxide generated in step (c) after step (c).

14. The preparation method of claim 7, further comprising:
    (d) firing after step (c).

15. The preparation method of claim 14, wherein the firing is performed at a temperature range of 500° C. to 700° C.

16. A catalyst including the composite of claim 1.

* * * * *